United States Patent [19]
Hoffmann et al.

[11] 4,076,748
[45] Feb. 28, 1978

[54] POLYCYCLIC SCENTS

[75] Inventors: Werner Hoffmann, Neuhofen; Karl von Fraunberg, Bobenheim, both of Germany

[73] Assignee: BASF Aktiengesellschaft, Ludwigshafen, Germany

[21] Appl. No.: 708,994

[22] Filed: Jul. 26, 1976

[51] Int. Cl.$^2$ ............................................. C07C 49/36
[52] U.S. Cl. ................................. 260/586 F; 260/598; 252/522; 260/617 F; 260/464; 260/346.3; 260/514 G; 560/116
[58] Field of Search ............... 260/586 F, 586 G, 598, 260/468 G; 252/522, 322

[56] References Cited
U.S. PATENT DOCUMENTS

| | | | |
|---|---|---|---|
| 3,852,358 | 12/1974 | Hall et al. | 260/586 F |
| 3,968,070 | 7/1976 | Sundt | 260/586 F |

OTHER PUBLICATIONS

Sauer, Angew Chem Int Edn, vol. 6, pp. 16–33 (1967).

*Primary Examiner*—James O. Thomas, Jr.
*Assistant Examiner*—James H. Reamer
*Attorney, Agent, or Firm*—Keil, Thompson & Shurtleff

[57] ABSTRACT

New polycyclic Diels-Alder adducts which are formed on reaction of 8-vinyl-tricyclo-[5,2,1,0$^{2,6}$]-dec-8-ene or 8-hydroxy-8-vinyl-tricyclo-[5,2,1,0$^{2,6}$]-decane with alkenes or alkynes having one or two activating substituents, e.g., —COOH, —COOCH$_3$, —COOC$_2$H$_5$, —CHO, —COCH$_3$, —COC$_2$H$_5$ or —CN. They have green, fresh, fruity and in some cases woody odors with long-lasting tenacity and/or fixing properties. They can be used as constituents of perfumes and of compositions for perfuming body care products, detergents and other consumer products.

4 Claims, No Drawings

POLYCYCLIC SCENTS

The present invention relates to Diels-Adler adducts of the general formula I

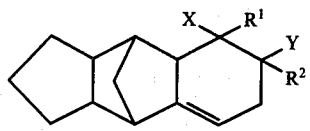

where $R^1$ and $R^2$ are —H or —$CH_3$, or $R^1$ and $R^2$ together are a further bond between the carbon atoms on which they are present, and X and Y are each —$CH_2OH$, —CH(OH)—$CH_3$, —COOH, —$COOCH_3$, —$COOC_2H_5$, —CHO, —CO—$CH_3$, —CO—$C_2H_5$ or —CN, or X and Y together are —CO—O—CO—, or one of X or Y is —H or —$CH_3$ and the other has one of the above meanings.

The new polycyclic Diels-Alder adducts are distinguished by valuable scent characteristics. They have green, fresh, fruity and in some cases woody odors with long-lasting tenacity and/or fixing properties. They may be used as constituents of perfumes and of compositions for perfuming body care products, e.g. soaps, shampoos and hair lotions, detergents and other consumer products. Furthermore, they may be used for flavoring foodstuffs and tobacco.

The present invention further relates to a process for the manufacture of the new compounds of the formula I, wherein the new 8-vinyl-tricyclo-[5,2,1,0$^{2,6}$]-dec-8-ene of the formula II

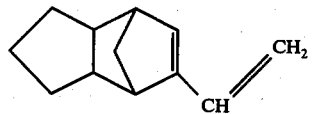

is subjected to a Diels-Alder reaction, by conventional methods, with a dienophile of the general formula III

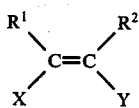

is $R^1$ and $R^2$ are —H or —$CH_3$ or $R^1$ and $R^2$ together are a further bond between the carbon atoms on which they are present and X and Y are each —COOH, —$COOCH_3$, —$COOC_2H_5$, —CHO, —$COCH_3$, —$COC_2H_5$ or —CN, or X and Y together are —CO—O—CO—, or one of X and Y is —H or —$CH_3$ and the other has one of the above meanings.

The new Diels-Alder adducts of the formula I, in which $R^1$ and $R^2$ are —H or —$CH_3$ and one of X or Y is —$CH_2OH$ or —CH(OH)—$CH_3$ and the other is H, are obtained by reducing the corresponding oxo compounds by conventional methods.

8-Vinyl-tricyclo-[5,2,1,0$^{2,6}$]-dec-8-ene, required as a starting compound, can be manufactured by a simple conventional method, by elimination of water from 8-vinyl-tricyclo-[5,2,1,0$^{2,6}$]-decan-8-ol, which in turn can be obtained by reacting tricyclo-[5,2,1,0$^{2,6}$]-decan-8-one, which is readily accessible, with a vinyl-magnesium halide by the Grignard method. Instead of the diene II, 8-vinyl-tricyclo-[5,2,1,0$^{2,6}$]-decan-8-ol can be used as the starting material, but this requires more severe reaction conditions, e.g. higher temperatures and/or acid catalysts, and the yields are therefore frequently less.

Suitable dienophiles of the formula III are:

a. Alkenes having only one activating substituent, i.e. compounds of the formula III, where $R^1$ and $R^2$ are —H or —$CH_3$, one of X or Y is —COOH, —$COOCH_3$, —$COOC_2H_5$, —CHO, —CO—$CH_3$, —CO—$C_2H_5$ or —CN and the other X or Y is —H, i.e. mono-$\alpha,\beta$-unsaturated aldehydes, ketones, nitriles, carboxylic acids or carboxylic acid esters. Examples which may be mentioned are acrolein, methacrolein, crotonaldehyde, methyl vinyl ketone, pent-2-en-4-one, acrylonitrile, methacrylonitrile, crotononitrile, acrylic acid, methacrylic acid, crotonic acid and the methyl esters and ethyl esters of the said 3 acids. The above aldehydes, ketones and nitriles are preferred.

b. Alkenes with two activating substituents, i.e. compounds of the formula III, where $R^1$ and $R^2$ are —H or —$CH_3$, especially —H, and X and Y are each —COOH, —$COOCH_3$, —$COOC_2H_5$, —CHO, —CO—$CH_3$, —CO—$C_2H_5$ or —CN, or X and Y together are —CO—O—CO—. Examples which may be mentioned are dimethyl fumarate, diethyl fumarate and maleic anhydride.

c. Alkylenes with only one activating substituent, i.e. compounds of the formula III, where $R^1$ and $R^2$ together are a further bond between the carbon atoms on which they are present, one of X or Y is —COOH, —$COOCH_3$, —$COOC_2H_5$, —CHO, —CO—$CH_3$, —CO—$C_2H_5$ or —CN and the other is —H or —$CH_3$. Examples which may be mentioned are propiolaldehyde (propynal), butyn-2-al, propiolic acid, tetrolic acid (butyn-2-oic acid), and the methyl esters and ethyl esters of the said acids.

d. Alkynes with two activating substituents, i.e. compounds of the formula III, where $R^1$ and $R^2$ together are a further bond between the carbon atoms on which they are present and X and Y are each —COOH, —$COOCH_3$, —$COOC_2H_5$, —CHO, —CO—$CH_3$, —CO—$C_2H_5$ or —CN. Examples which may be mentioned are acetylenedicarboxylic acid and its methyl and ethyl esters.

The dienophiles of the formula III are, in general, known and commercial compounds.

Preferably, the alkenes with only one actuating substituent, described under a), are used as dienophiles of the formula III.

In general, the Diels-Alder reaction is carried out by bringing a mixture of 8-vinyl-tricyclo-[5,2,1,0$^{2,6}$]-dec-8-ene (II), the dienophile of the formula III and, if appropriate, an inert solvent, to from 0° to 150° C, preferably from 30° to 80° C, for the length of the reaction time. The latter is from about 1 to 200 hours, depending on the nature of the dienophile. The dienophile is in general used in from about 0.5 to 10 molar amount, preferably in from about 2 to 5 molar amount, based on II.

To avoid possible resinification reactions, a small amount, i.e. from about 10 to 100 mg per mole of II, of a conventional stabilizer for Diels-Alder reactions, e.g. hydroquinone, is generally added to the reaction mixture.

The reaction may be carried out in the absence of solvents or in an inert solvent.

Examples of inert solvents which can be used are aliphatic hydrocarbons, e.g. pentane, hexane, cyclohexane and hydrocarbon fractions, aromatic hydrocarbons, e.g. benzene, toluene or xylene, chlorohydrocarbons, e.g. methylene chloride, chloroform or chlorobenzene, ethers, e.g. diethyl ether, dipropyl ether, diisopropyl ether, tetrahydrofuran and anisole, alcohols, e.g. methanol, ethanol, propanol, isopropanol and cyclohexanol, ketones, e.g. acetone, methyl ethyl ketone and methyl isopropyl ketone, amides, e.g. dimethylformamide, dimethylacetamide and hexamethylphosphotriamide or nitro compounds, e.g. nitromethane and nitrobenzene, or mixtures of the said solvents.

The reaction is either carried out at atmospheric pressure or under the autogenic pressure of the reactants in closed reaction vessels.

The reaction mixture is worked up by conventional methods, e.g. by distillation.

Regarding further details of Diels-Alder reactions, reference may be made to R. Sauer, Angew. Chem. 79 (1967), 77–94.

The Diels-Alder adducts are in general obtained as mixtures of different isomers. When using unsymmetrical olefins of the formula III, 8 stereoisomeric Diels-Alder adducts are possible, depending on the steric course of the addition reaction. The dienophile can attack "meta" or "ortho" to the $C_9$ of the diene of the formula II, "exo" or "endo" and from above or from below. The general rules of the Diels-Alder reaction and analogous examples with vinyl cyclohexenes or vinyl-bicylenes (see A. S. Onishchenko "Diene Synthesis", Israel Program for Scientific Translation, Jerusalem 1964, pages 410–445, especially pages 410–413 and pages 423–425) lead to the expectation that the main product would be the "ortho-endo" isomer, i.e. in the case of acrolein the isomers

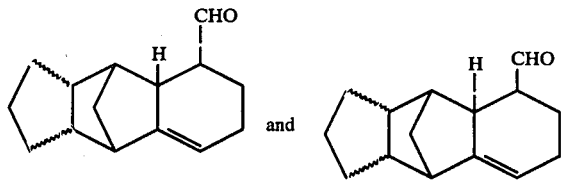

with the attack "from below" in the former case and "from above" in the latter. A prediction of the actual attack is difficult, given the complicated stereochemistry of the diene, and is decisively dependent on the exo/endo configuration of the 5-membered ring. If symmetrical olefins and alkynes are used as dienophiles of the formula III, the number of possible stereoisomers is less.

The stereoselectivity of the reaction can be increased by using very low reaction temperatures and/or by adding catalytic amounts of Lewis acids, e.g. $BF_3$, $AlCl_3$, $ZnCl_2$ and the like (1.c., especially page 84).

If the reaction is carried out in the presence of catalytic amounts of a Lewis acid such as $AlCl_3$, $BF_3$, $SnCl_4$ or $ZnCl_2$, the procedure followed is that described above, but at lower temperatures, i.e. at from about $-80°$ to $+20°$ C, preferably from $-40°$ to $0°$ C. The amount of catalyst is from 0.1 to 10%, preferably from 0.5 to 5%, based on II employed.

Carbonyl compounds can be reduced to the alcohols in accordance with numerous standard processes, e.g. by catalytic hydrogenation, by reduction with metals or metal hydrides or by electrochemical or photochemical reduction. Regarding further details, reference may be made to S. Patai, "The Chemistry of the Hydroxyl Group", Interscience Publishers 1971, pages 231–243.

Example 3 describes the reduction of a carbonyl compound with a metal hydride ($NaBH_4$).

The new polycyclic Diels-Alder adducts are distinguished by valuable scent properties. They have green, fresh, fruity and in some cases woody scents with long-lasting tenacity. Furthermore, they possess fixing properties. Accordingly, they can be used as constituents of perfumes and of compositions for perfuming body care products, e.g. soaps, shampoos and hair lotions, detergents and other consumer products. The scent depends somewhat on the stereochemistry (exo/endo ratio) of the tricyclo-[5,2,1,0$^{2,6}$]-decan-8-one employed, but in general it is satisfactory to use the adducts obtained from the commercial ketone.

EXAMPLE 1

16.0 g (0.10 mole) of 8-vinyl-tricyclo-[5,2,1,0$^{2,6}$]-dec-8-ene, 11.2 g (0.2 mole) of acrolein, 10 mg of hydroquinone and 100 ml of toluene are kept at 90° C for 3 hours. The reaction product is washed with three 50 ml portions of water and is then distilled. 19.2 g (89% of theory) of an aldehyde mixture pass over at from 110° to 115° C/0.1 mm Hg.

$n_D^{25}$: 1.5332.

Scent: waxy, green-pod-like, peach, fixing.

The gas chromatogram shows 2 compounds in the ratio of 89 : 11. The $^1H$ nuclear resonance spectrum shows 2 aldehyde signals at δ 9.60 and 9.69 in the ratio of 85 : 15, as well as several minor signals, and also an olefinic proton at δ 5.34. The analysis and molecular weight are in agreement with the empirical formula. The $^{13}C$ spectrum suggests that the main component probably has structure I with $R^1$ and $R^2$ = —H, X = —CHO and Y = —H.

EXAMPLE 2

16 g (0.1 mole) of 8-vinyl-tricyclo-[5,2,1,0$^{2,6}$]-dec-8-ene, 11.2 g (0.2 mole) of acrolein, 50 ml of toluene and 10 mg of hydroquinone are kept for 150 hours at from 20° to 25° C. On working up as described in Example 1, 19.4 g (90% of theory) of an aldehyde mixture are obtained, which, according to gas chromatography and nuclear resonance spectroscopy, contains the same two aldehydes as in Example 1, but in the ratio of 92.5 : 7.5.

EXAMPLE 3

A solution of 21.6 g (0.1 mole) of the aldehyde mixture obtained in Example 1, in 30 ml of ethanol, is added to 4 g of sodium borohydride in 200 ml of ethanol in the course of 60 minutes at 25° C and the reaction mixture is then stirred for 3 hours at 25° C. The ethanol is then distilled off, the residue is taken up in ether and acidified to pH 3 with 10 percent strength sulfuric acid, and the organic phase is concentrated and distilled. At from 111° to 115° C/0.5 mm Hg, 16.2 g (74% of theory) of an alcohol pass over, which alcohol, according to the analytical data and the nuclear resonance spectrum, probably has the formula I, where $R^1$, $R^2$ and Y are —H and X is —CH$_2$OH.

$n_D^{25}$: 1.5368.

Scent: resembling the aldehyde, fainter but with substantially more persistent tenacity.

EXAMPLE 4

21.6 g (0.1 mole) of the aldehyde mixture obtained according to Example 1, 50 ml of methanol and 1 g of Raney nickel are treated with hydrogen at 100° C and 100 atmospheres pressure, unitl the absorption of hydrogen has ceased. On subsequently working up the mixture by distillation, 19.8 g of an alcohol mixture distil at from 135° to 136° C/0.1 mm Hg, and solidify to a wax; according to the analytical data and the $^1$H and $^{13}$C nuclear resonance spectrum, the main product (about 80%) of the mixture has the structure

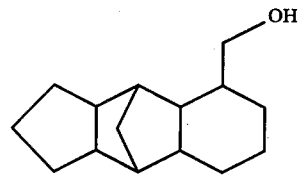

$n_D^{25}$: 1.5285.
The yield is 95% of theory.

EXAMPLE 5

A solution of 8.0 g (0.05 mole) of 8-vinyl-tricyclo-[5,2,1,0$^{2,6}$]-dec-8-ene, 10.6 g (0.2 mole) of acrylonitrile, 50 ml of toluene and 10 mg of hydroquinone is heated at 80° C for 12 hours. The reaction mixture is then cooled, washed with twice 30 ml of water, concentrated and distilled. 8.1 g (corresponding to 76% of theory) of an 80 : 20 mixture of nitriles pass over at from 125° to 128° C/0.2 mm Hg. From the analytical and spectroscopic data, the main product probably has the formula I, where $R^1$, $R^2$ and Y are —H and X is —CN.

$n_D^{25}$: 1.5325.
Scent: fresh, flowery, slightly fruity (lime), good tenacity.

EXAMPLE 6

Following the procedure described in Example 5, but using 0.2 mole of crotonaldehyde instead of 0.2 mole of acrylonitrile, 7.2 g (corresponding to 62.5% of theory) of a Diels-Alder adduct of the formula I, where $R^1$ and $R^2$ are —H and one of X or Y iz —CH$_3$ and the other is —CHO are obtained; the product boils at from 112° to 115° C/0.05 mm Hg and its refractive index $n_D^{25}$ is 1.5290.

Scent: coniferous, woody, suggestion of vetiver oil, good tenacity.

EXAMPLE 7

Following the procedure described in Example 5, but using 0.2 mole of methacrolein instead of 0.2 mole of acrylonitrile, 8.3 g (corresponding to 72% of theory) of a Diels-Alder adduct of the formula I, where $R^2$ is —CH$_3$, Y is —CHO and X and $R^1$ are —H, or $R^1$ is —CH$_3$, X is —CHO and $R^2$ and Y are —H are obtained; the product boils at from 105° to 106° C/0.05 mm Hg and its refractive index $n_D^{25}$ is 1.5292.

Scent: pine-like, woody, fresh, slightly fruity.

EXAMPLE 8

Following the procedure described in Example 5, but using 0.2 mole of ethyl acrylate instead of 0.2 mole of acrylonitrile, 9.5 g (corresponding to 73% of theory) of a Diels-Alder adduct of the formula I, where one of X or Y is —COOC$_2$H$_5$ and the remaining radicals are —H are obtained; the product boils at from 117° to 121° C/0.05 mm Hg and its refractive index $n_D^{25}$ is 1.5152.

Scent: faintly mint-like, green.

EXAMPLE 9

Following the procedure described in Example 5, but using 0.2 mole of methyl vinyl ketone instead of 0.2 mole of acrylonitrile, 10.8 g (corresponding to 94% of theory) of a Diels-Alder adduct of the formula I, where one of X or Y is —CO—CH$_3$ and the remaining radicals are —H are obtained; the product boils at from 115° to 120° C/0.05 mm Hg and its refractive index $n_D^{25}$ is 1.5259.

Scent: herbacious, fruity (raspberries), earthy, good tenacity.

EXAMPLE 10

Following the procedure described in Example 5, but using 0.2 mole of ethyl propiolate instead of 0.2 mole of acrylonitrile, 9.2 g (corresponding to 71% of theory) of a Diels-Alder adduct of the formula I, where $R^1$ and $R^2$ form a further bond, Y is H and X is COOC$_2$H$_5$ are obtained; the product boils at from 128° to 130° C/0.1 mm Hg and its refractive index $n_D^{25}$ is 1.5334.

Scent: faint, musty.

EXAMPLE 11

16 g (0.1 mole) of 8-vinyl-tricyclo-[5,2,1,0$^{2,6}$]-dec-8-ene, 19.6 g (0.2 mole) of maleic anhydride, 50 ml of toluene and 10 mg of hydroquinone are kept at from 20° to 25° C for 70 hours. On working up the mixture as described in Example 1, 9.5 g (corresponding to 75.5% of theory) of a Diels-Alder adduct of the formula I, where X and Y are —COOH and $R^1$ and $R^2$ are —H, are obtained; the product boils at from 153° to 157° C/0.05 mm Hg, its $n_D^{25}$ = 1.5412, and it possesses good fixing properties.

EXAMPLE 12

17.8 g (0.1 mole) of 8-vinyl-tricyclo-[5,2,1,0$^{2,6}$]-decan-8-ol, 19.6 g (0.2 mole) of maleic anhydride and 80 ml of xylene are heated at 160°–180° C for 5 hours. Working up of the reaction mixture as described in Example 1 gives 18.2 g (corresponding to 68% of theory) of an adduct boiling at from 158° to 163° C/0.05 mm Hg.

What we claim is:
1. A Diels-Alder adduct of the formula

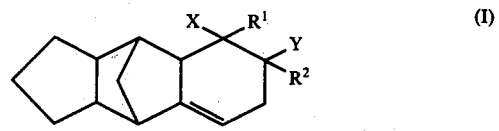

where $R^1$ and $R^2$ are independently —H or —CH$_3$, or $R^1$ and $R^2$ together are a further bond between the carbon atoms on which they are present, one of X and Y is —H or —CH$_3$ and the other is —COOH$_3$, —COOC$_2$H$_5$, —CHO, —CO —CH$_3$, or —CO —C$_2$H$_5$.

2. A Diels-Alder adduct of the formula I

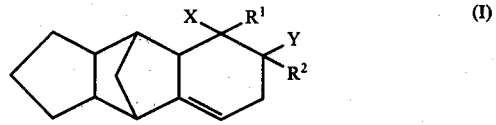

where $R^1$ and $R^2$ are independently —H or —CH$_3$, one of X and Y is —CHO, —CO —CH$_3$ or —CO —C$_2$H$_5$ and the other is —H or —CH$_3$.

3. A Diels-Alder adduct as set forth in claim 1, wherein one of X and Y is —H or —CH$_3$ and the other is —COOCH$_3$, —COOC$_2$H$_5$, —CHO, —CO —CH$_3$ or —CO —C$_2$H$_5$.

4. A Diels-Alder adduct as set forth in claim 1, wherein one of X and Y is —H or —CH$_3$ and the other is —CHO, —CO —CH$_3$ or —CO —C$_2$H$_5$.

* * * * *

UNITED STATES PATENT AND TRADEMARK OFFICE
CERTIFICATE OF CORRECTION

PATENT NO. : 4,076,748
DATED : February 28, 1978
INVENTOR(S) : Werner Hoffmann et al It is certified that error appears in the above—identified patent and that said Letters Patent are hereby corrected as shown below:

First page, left-hand column, line 9, insert

--[30] Foreign Application Priority Data
September 1, 1975   Germany . . . .   25 38 790 --.

Signed and Sealed this

Twenty-sixth Day of December 1978

[SEAL]

Attest:

RUTH C. MASON
*Attesting Officer*

DONALD W. BANNER
*Commissioner of Patents and Trademarks*